United States Patent [19]

Chou et al.

[11] 4,335,961
[45] Jun. 22, 1982

[54] REFRACTIVE INDEX MEASUREMENT OF OPTICAL THIN-FILM

[75] Inventors: Tzeyang J. Chou, Liverpool, N.Y.; Oded Arnon, Givataim, Israel

[73] Assignee: Inficon Leybold-Heraeus, East Syracuse, N.Y.

[21] Appl. No.: 141,428

[22] Filed: Apr. 18, 1980

[51] Int. Cl.³ .......................................... G01N 21/45
[52] U.S. Cl. ..................................... 356/361; 356/128
[58] Field of Search ........................ 356/128, 382, 361

[56] References Cited

U.S. PATENT DOCUMENTS 3,751,643  8/1973  Dill et al. ............................ 364/582
3,892,490  7/1975  Uetsuki et al. ...................... 356/382

OTHER PUBLICATIONS

"The Determination of the Refractive Index and Thickness of Transparent Film"; Khawaja, J. Phys. D.: Appl. Phys., vol. 9, 1976, pp. 1939-1943.

*Primary Examiner*—Vincent P. McGraw
*Attorney, Agent, or Firm*—Bruns & Jenney

[57] ABSTRACT

Method and apparatus for determining the refractive index of an optical film over a wide spectral range is described that involves measuring the changing radiant reflectance (or transmittance) of the film at various wavelengths as it is being deposited upon a substrate, as for example by vacuum deposition process. By determining the values of the extreme limits, an envelope of the peak reflectance can be developed from which the film's index of refraction is obtained over the entire spectral range that is situated between the two extreme wavelength channels.

9 Claims, 3 Drawing Figures

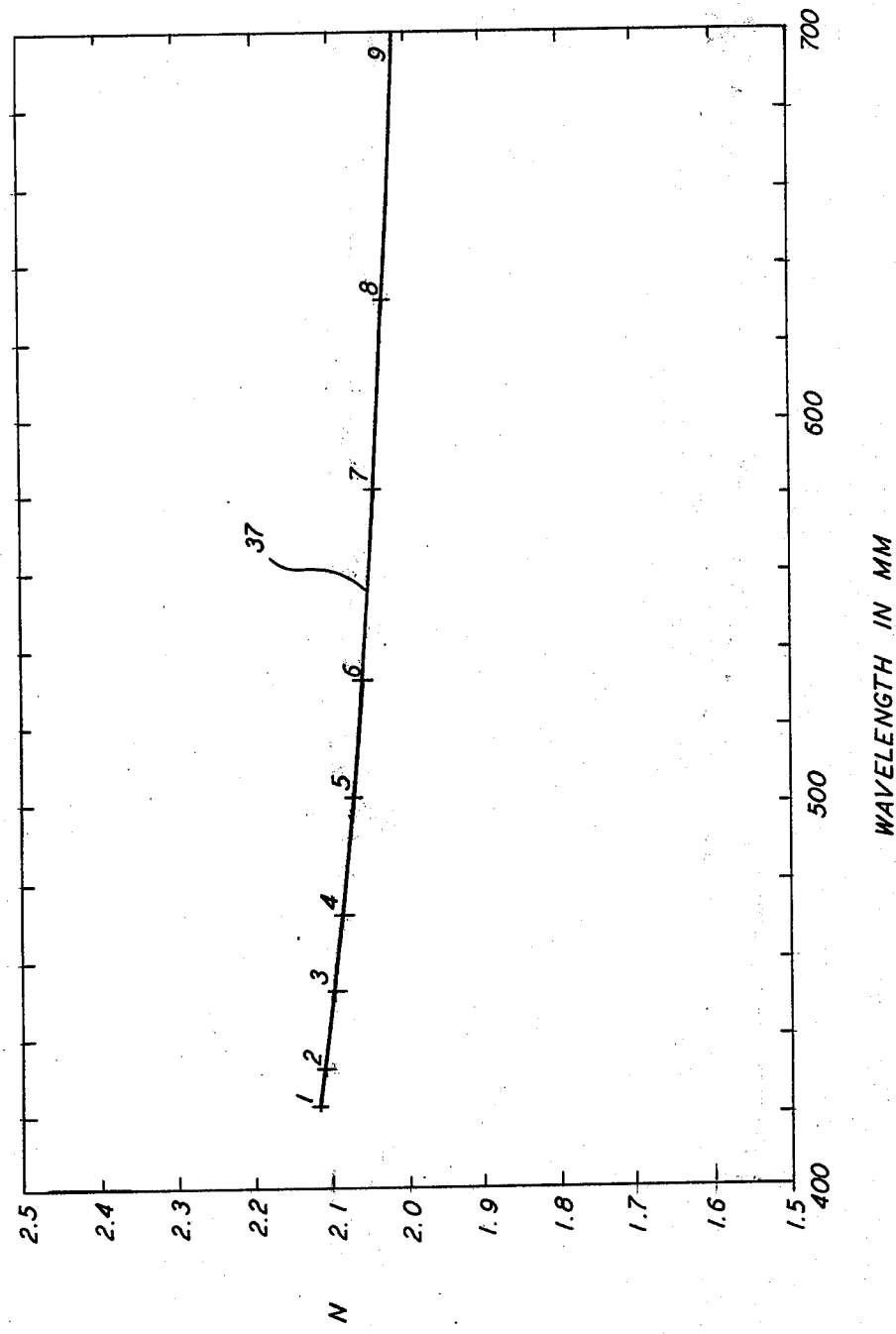

REFRACTIVE INDEX MEASUREMENT OF OPTICAL THIN-FILM

BACKGROUND OF THE INVENTION

This invention relates to optical interference filters and, in particular, to means for measuring the refractive index of an optical film over a broad spectral range as the film is being deposited upon a substrate.

Most optical films are produced in a vacuum deposition chamber wherein the coating material is evaporated and then allowed to condense upon a substrate under closely controlled conditions. Production problems, however, are encountered in the deposition process that may adversely affect the accuracy and repeatability with which single or multilayered filters are produced. To a great extent some of these difficulties can be avoided or overcome if the index of refraction of the film can be determined over the spectral range of interest during the time that film is growing within the vacuum chamber. By being able to rapidly and accurately determine this particular property, which is sometimes referred to as the "vacuum index", the data can be used to closely control the fabrication process.

In U.S. Pat. No. 3,892,490, a method for producing multi-layered filters is described which is designed to minimize the reflectance of a lens system used in a camera. In the process, the reflectance of each coating is monitored at one preselected wavelength as the coating grows and a resultant time-based curve is compared to a second curve depicting optimum conditions. Variances between the two curves are used to provide a basis under which adjustments to the system can be made. As only one wavelength is monitored during the growth of each layer, the described procedure cannot be used to discern the index of refraction of the film over a range of wavelengths.

SUMMARY OF THE INVENTION

It is therefore an object of the present invention to provide an improved method for determining the dispersive index of refraction of an optical film over a broad spectral range.

Another object of the present invention is to determine the index of refraction of a thin-film in real time while the film is being deposited upon a substrate.

Yet another object of the present invention is to provide information concerning perturbations by residual absorption and/or index inhomogeneity of the deposited film, while it is still inside the vacuum chamber.

A further object of the present invention is to simplify the means for determining the refractive index of a single layer optical thin-film over a broad spectral range.

These and other objects of the present invention are attained by scanning an optical film as it is being deposited upon a substrate with electromagnetic radiation at a plurality of discrete wavelength channels, measuring the reflectance or transmittance of the film at each channel as the film grows, identifying the peak limits of reflectance or transmittance, and determining the index of refraction for each wavelength upon the measured data.

BRIEF DESCRIPTION OF THE DRAWINGS

For a better understanding of these and other objects of the present invention, reference is had to the following detailed description of the invention that is to be read in conjunction with the accompanying drawings, wherein:

FIG. 3 is a resultant plot of the measured index of refraction versus wavelength for the wavelengths shown in FIG. 2.

DESCRIPTION OF THE INVENTION

The present invention involves a technique for the in situ determination of the refractive index of an optical film over a relatively wide spectral range during the time the film is being deposited upon a substrate. The resultant value of the vacuum index is useful for vacuum processes such as monitoring or controlling the deposition of optical interference filters.

As is well known in the art, when a film is being deposited upon a substrate, the reflectance and/or transmittance of the film changes periodically as its thickness increases. In the case where the film index is greater than that of the substrate, the reflectance at a given wavelength $\lambda$ reaches the peak value for the first time when the optical thickness of the film is equal to one-quarter of the given wavelength:

$$nd = \lambda/4 \qquad (1)$$

where:

n is the index of refraction of the film at the given wavelength $\lambda$; and d is the physical thickness of the film.

This relationship is typically used in practice to greatly simplify problems involved in the design and manufacture of thin film devices.

It can be shown that the value of the peak reflectance Rp can be expressed in terms of the film and the substrate indices only:

$$Rp(\lambda) = \left[ \frac{n_s(\lambda) - n^2(\lambda)}{n_s(\lambda) + n^2(\lambda)} \right]^2 \qquad (2)$$

where:

Rp is the measured peak reflectance for the subject wavelength ($\lambda$);

$n_s$ is the index of refraction of the substrate at the subject wavelength; and n is the index of refraction of the film at the subject wavelength.

From the above relationship it should be apparent that once the index of the substrate is known and the peak reflectance is measured, the index of the film can be easily calculated.

Figure 2:
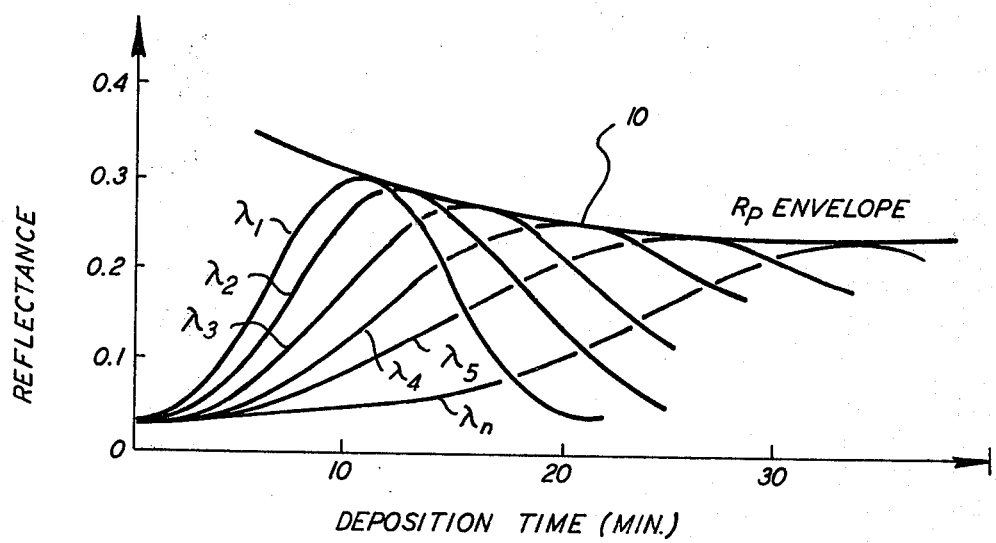
FIG. 2 is a schematic plot of reflectance versus deposition time for various wavelengths.

Although the noted relationship provides the index value at only a single wavelength, it can be used during the vacuum deposition process to measure the dispersive index of a film over a wide spectral range in the manner to be explained below. In practice, the film as it is growing in the chamber, is scanned by electromagnetic radiation, typically being light energy, at a number of different wavelength channels within a preselected range and the peak limit value for each wavelength is measured. The term wavelength channel as herein used refers to a particular spectral wavelength or waveband as typically produced by an interference filter or the like wherein an extremely narrow spectrum of radiation is provided. As illustrated by the diagram in FIG. 2, the peak reflectance (Rp) for each wavelength is independent of the others. As the physical thickness of the film increases during the deposition period, the measured peak reflectance for each wavelength $\lambda_1, \lambda_2 - \lambda_n$ is arrived at in an ordered time sequence that is dependent upon the relative position of the wavelength in the spectral range. A curve 10 depicting the peak reflectances of a group of wavelengths situated within the subject spectral range can be plotted to provide an envelope from which the index of refraction for all wavelengths between the two extreme measured wavelength channels may be derived in accordance with relationship (2) noted above.

Figure 1:
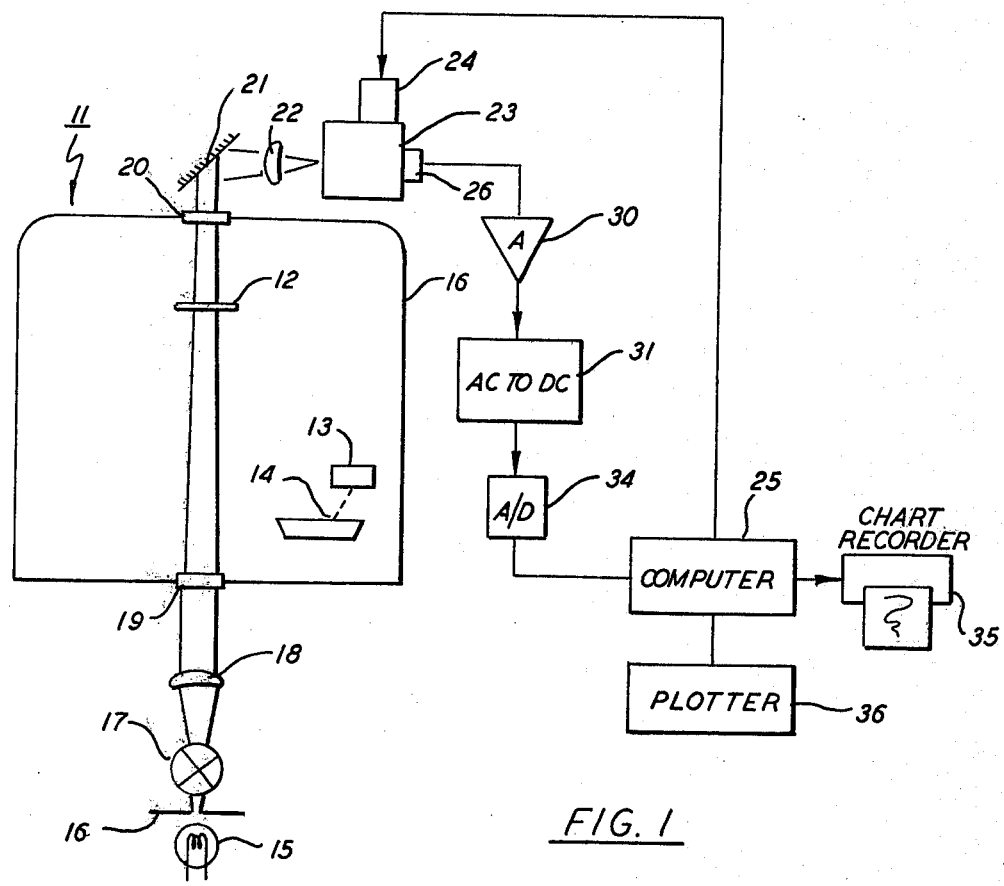
FIG. 1 is a schematic drawing of a monitoring system embodying the teachings of the present invention used in conjunction with equipment for vacuum depositing an optical film upon a substrate.

As illustrated in FIG. 1, the present technique was reduced to practice in a Leybold-Heraeus A700Q vacuum coating system 11 by depositing a single layer of tertiary zirconium-titanium-oxygen mixture upon a fresh glass substrate 12. In the coater, the test glass substrate temperature was sensed by a thermocouple (not shown) and was maintained at 250° C. under closed loop conditions. A base pressure of $2 \times 10^{-6}$ mbar was established in the chamber and the pressure raised by two decades after admitting oxygen to the chamber by means of a needle valve. An Inficon 1C-6000 deposition controller 13 was utilized to regulate the condensation rate of the coating material contained in crucible 14 at a constant level of 1 Angstrom per second. A constant acceleration voltage of 5.5 KV was used to produce evaporation with the electron beam being swept and defocused over the evaporant to minimize dissociation of the material.

The coating system was set up to monitor and measure the film's transmittance at normal incidence. The apparatus consisted of a tungsten quartz halogen light source 15 that was arranged to direct the light through a pinhole 16, a chopper 17, a lens 18 and a window 19 at the glass substrate 12 situated within the vacuum chamber 11.

The transmitted light passes out of the chamber through another window 20 and reaches a grating monochromator 29 after being reflected by the mirror 21 and converged by the lens 22. The monochromator was driven by a stepping motor 24 under the control of a computer 25, to scan the spectral range between 400 to 700 nm. With that arrangement a wavelength accuracy within 1 nm with resolution of 4 nm was obtained.

A photovoltaic detector 26 having high linearity over a wide dynamic range was positioned adjacent to the exit slit of the monochromator. It received the light intensity transmitted through the glass substrate at each of the discrete wavelength channels over the noted scanning range.

The output signal of the detector was fed to a tuned amplifier 30 set to the system chopping frequency and then on to a fast response ac to dc converter 31. The dc output of the converter was applied to an analogue to digital converter 34 before being passed on to the computer 25 for processing.

Before commencing the film deposition process, nine wavelength channels equally spaced along the $1/\lambda^2$ scale within the spectral range of interest were selected for interrogation and the computer programmed to regulate the activity of the monochromator and the detector in response thereto. The transmitted flux through the fresh substrate was then initially recorded for all wavelength channels to permit the light readings to be corrected for substrate. The deposition process was then commenced and the channels scanned at the substrate once every four seconds. Accordingly, the film's transmittance, which was corrected for back side reflection, was continually measured for all channels as the film grew, thereby providing a time history sequence for each channel. A minimum peak value detection of the transmitted energy was performed by the computer to calculate the index of refraction for each of the selected channels based upon the measured data.

The deposition of the film continued even beyond the minimum peak transmittance was obtained at the longest wavelength channel. In fact, the deposition was terminated only after the optical thickness of the film reached the halfwave point at the shortest wavelength channel. At that thickness the transmittance is expected to get the same value as the uncoated substrate. This principle was used to ensure that the deposited film is absorption-free and homogeneous. A chart-recorder 35 was used to record the changing transmittance of the film during the deposition time at the shortest wavelength channel.

After processing the data, the index of refraction value was plotted on an X-Y plotter 36 for each of the nine wavelength channels. In practice, it has been found advantageous to curve-fit these values to a dispersion polimial. The Selmeir dispersion relationship in the form:

$$n^2(\lambda) = A + B/\lambda^2$$

has been found suitable to represent the experimental results wherein the terms A and B are constant coefficients.

The nine discrete measured values of the index, along with the corresponding best fitted curve 37 are shown in FIG. 3. They represent the measured index over the spectral range between the two extreme channels.

To test reproducibility, six single layer titanium-oxide films of halfwave optical thickness at 420 nm were deposited upon a substrate from six different crucibles in six runs keeping all evaporation conditions constant. A reproducibility index of better than $\pm 1.05\%$ was obtained over a spectral range of between 420 and 700 nm. No difference was noted in the results of the runs. A second test in which five single layer tantalum oxide films of halfwave optical thickness at 400 nm was deposited out of a single crucible under identical conditions. Again, no significant index deviation between layers was discernable. An index variation of about $\pm 1.51\%$ across the range was obtained.

While this invention has been described with reference to the details as set forth above, it is not limited to any special material, to any special spectral range or to the specific structure as disclosed. The invention is intended to cover any modifications or changes as may come within the scope of the following claims.

We claim:

1. The method of determining the refractive index of an optical film over a wide spectral range including the steps of depositing a film of material upon a substrate so that the thickness of the film increases with time, continually contacting the film with electromagnetic radiation as the film is being deposited upon the substrate so that the radiation is redirected by the contacted film, periodically changing the wavelength of the energy contacting the film between a plurality of wavelength channels that are situated within a predetermined spectral region, measuring the extreme limits of the radiation intensity redirected by the film for each channel, determining from the measured limits the refractive index for each wavelength channel, and plotting a curve of the determined indices to provide a profile of the film index over the entire predetermined range.

2. The method of claim 1 wherein the limits of the radiation reflected by the film are measured.

3. The method of claim 1 wherein the limits of the radiation transmitted by the film are measured.

4. The method of claim 1 further including the step of curve-fitting a dispersion polynomial to the determined refractive indices.

5. The method of claim 2 wherein the film's index of refraction is greater than that of the substrate and the limit of reflected radiation intensity for each channel occurs at a point where the optical thickness of the film is equal to one-quarter of the channel wavelength.

6. Apparatus for determining the refractive index of an optical film over a spectral range including deposition means for coating a substrate with an optical film whereby the film thickness is increased over a period of time, a light source arranged to direct a beam of light at the film as it is being deposited upon the substrate, scanning means for periodically changing the wavelength of the light contacting the film whereby the film is contacted by light within a plurality of discrete wavelength channels situated within a predetermined spectral range, detector means for measuring the limits of intensity of light within each channel that is positioned to intercept light redirected by the film, computer means operatively associated with the detector means for determining from the measured limits the index of refraction of the film for each channel within said spectral range, and means responsive to the computer means for providing a graphic representation of the index of refraction of the film over said spectral range.

7. The apparatus of claim 6 wherein the detector means is arranged to measure the intensity of light reflected by the film.

8. The apparatus of claim 6 wherein the detector means is arranged to measure the intensity of light transmitted by the film.

9. The apparatus of claim 6 wherein the scanning means is an optical monochromator that is driven by a stepping motor through the light beam to provide a selected number of wavelength channels within the spectral range.

* * * * *